United States Patent [19]
Patel

[11] Patent Number: 4,748,984
[45] Date of Patent: Jun. 7, 1988

[54] CATHETER ASSEMBLY AND METHOD OF PERFORMING CORONARY ANGIOGRAPHY AND ANGIOPLASTY

[76] Inventor: Piyush V. Patel, 3401 Salisbery, Midland, Tex. 79707

[21] Appl. No.: 55,534

[22] Filed: May 29, 1987

[51] Int. Cl.4 ............................................. A61M 25/00
[52] U.S. Cl. ..................................... 128/658; 128/344; 128/348.1; 604/280; 604/284
[58] Field of Search .................. 128/4, 8, 207.15, 343, 128/344, 348.1, 656–658; 604/52, 53, 95, 96–103, 170, 264, 280–284

[56] References Cited
U.S. PATENT DOCUMENTS

| | | | |
|---|---|---|---|
| 3,860,006 | 1/1975 | Patel | 604/281 |
| 4,619,247 | 10/1986 | Inoue et al. | 604/96 |
| 4,655,746 | 4/1987 | Daniels et al. | 604/101 |

FOREIGN PATENT DOCUMENTS 0268204  10/1929  Italy ........................................ 128/8

Primary Examiner—Dalton L. Truluck
Assistant Examiner—Frank Wilkens
Attorney, Agent, or Firm—Herbert J. Hammond

[57] ABSTRACT

A catheter assembly including a dilating catheter, a guiding catheter, and a length of tubing. The tubing is connected to the guiding catheter, and is pivotable between two positions. In the first position, the proximate end of the tubing is end to end with the tip of the catheter. In the second position, the proximate end of the tubing is adjacent the tip of the guiding catheter. The tubing has a plurality of side holes. A guide wire holds the tubing in the first position. The catheter assembly is inserted into the patient's aorta, while the tubing is in the first position. The guide wire is removed, and the tubing is pivoted to the second position. The proximate end of the tubing and the tip of the guiding catheter are then inserted into an artery. Angiography or angioplasty then proceeds normally.

12 Claims, 1 Drawing Sheet

CATHETER ASSEMBLY AND METHOD OF PERFORMING CORONARY ANGIOGRAPHY AND ANGIOPLASTY

BACKGROUND OF THE INVENTION

1. Field of the Invention

This invention relates in general to medical equipment and procedures. In particular, the invention relates to a catheter assembly and a method of using the catheter assembly to perform coronary angiography and coronary angioplasty.

2. Description of Related Art

Coronary angiography and angioplasty are very common medical procedures. Angiography involves the insertion of a dye into certain arteries as a diagnostic aid. Angioplasty is a procedure to open a coronary artery which has become partially blocked by a stenotic lesion, an abnormal narrowing of an artery due to injury or disease. Both procedures involve the insertion of a catheter into the aorta, by way of the femoral artery, under local anesthesia. The tip of the catheter is inserted into the opening of the coronary artery. A dye can then be injected through the catheter into the coronary arteries for coronary angiography.

To perform coronary angioplasty, a dilating catheter is passed through the guiding catheter into the coronary artery. The tip of the dilating catheter is passed through the stenotic lesion in the coronary artery. A balloon on the tip of the dilating catheter is then inflated with a fluid. The balloon forces the blockage open and enlarges the lumen, or passage, through the artery.

A problem may develop during angiography and angioplasty. The guiding catheter, inserted into the lumen of the coronary artery, may occlude the flow of blood into the coronary artery. If the coronary artery is occluded and dye is injected through the catheter, life threatening cardiac arrhythmia, such as ventricular tachycardia, ventricular fibrillation, cardiac arrest, or myocardial infarction, may result.

One method of perfusing blood past the tip of the guiding catheter into the coronary artery is by providing a side hole in the catheter. However, if there is a side hole in the catheter, pressures at the tip of the catheter can no longer be monitored. Further, dye can no longer be injected through the catheter into the coronary artery, because most of the dye will pass through the side hole, rather than through the tip of the catheter.

SUMMARY OF THE INVENTION

The catheter assembly of the invention overcomes the problem of perfusing blood past the tip of the guiding catheter by providing a length of tubing, pivotably connected to the guiding catheter. The tubing pivots between a first position, in which the proximate end of the tubing is end to end with the tip of the guiding catheter, and a second position, in which the proximate end of the tubing is adjacent to the tip of the guiding catheter.

A guide wire holds the length of tubing in the first position during the insertion of the guiding catheter into the body. The guide wire is then removed and the catheter is maneuvered to cause the length of tubing to pivot to the second position. The tip of the guiding catheter and the proximate end of tubing are then inserted into the ostium of the coronary artery.

The tubing has a plurality of side holes, which allow blood to perfuse through the tubing into the coronary artery. The tubing preferably has a curved shape, to give added support to the guiding catheter. The added support helps to prevent the guiding catheter from being forced out of the lumen of the coronary artery.

DESCRIPTION OF THE PREFERRED EMBODIMENT

Figure 1:
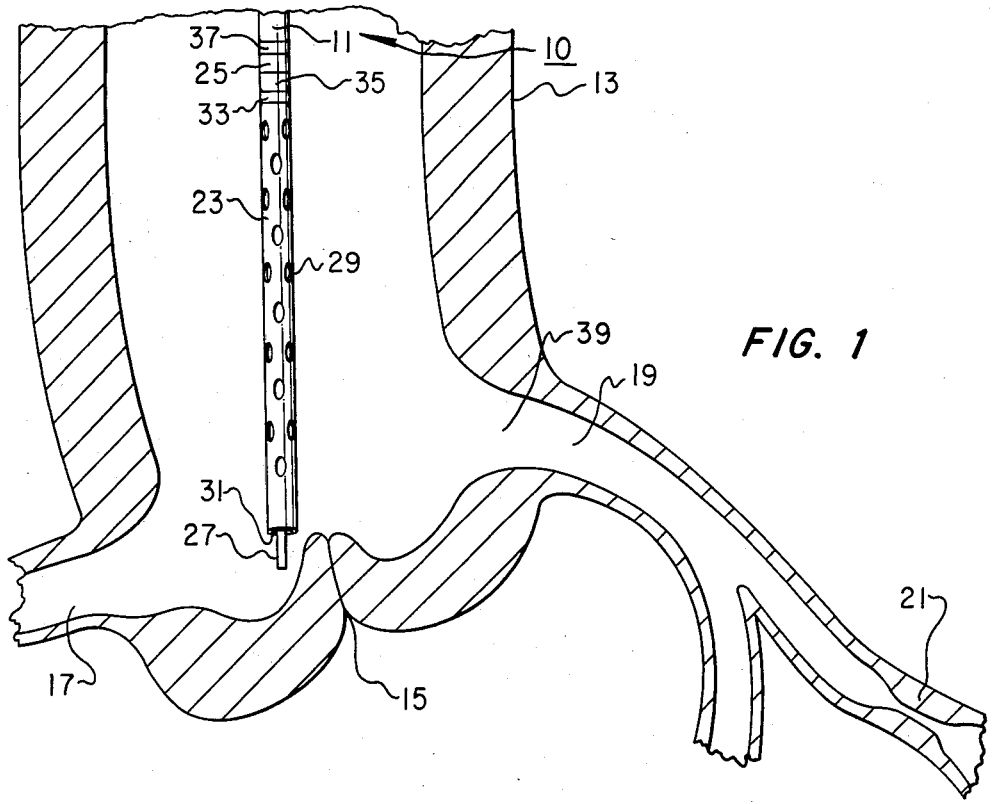
FIG. 1 is a side view of the catheter assembly of the invention, in which the tubing is shown in the first position.
Figure 2:
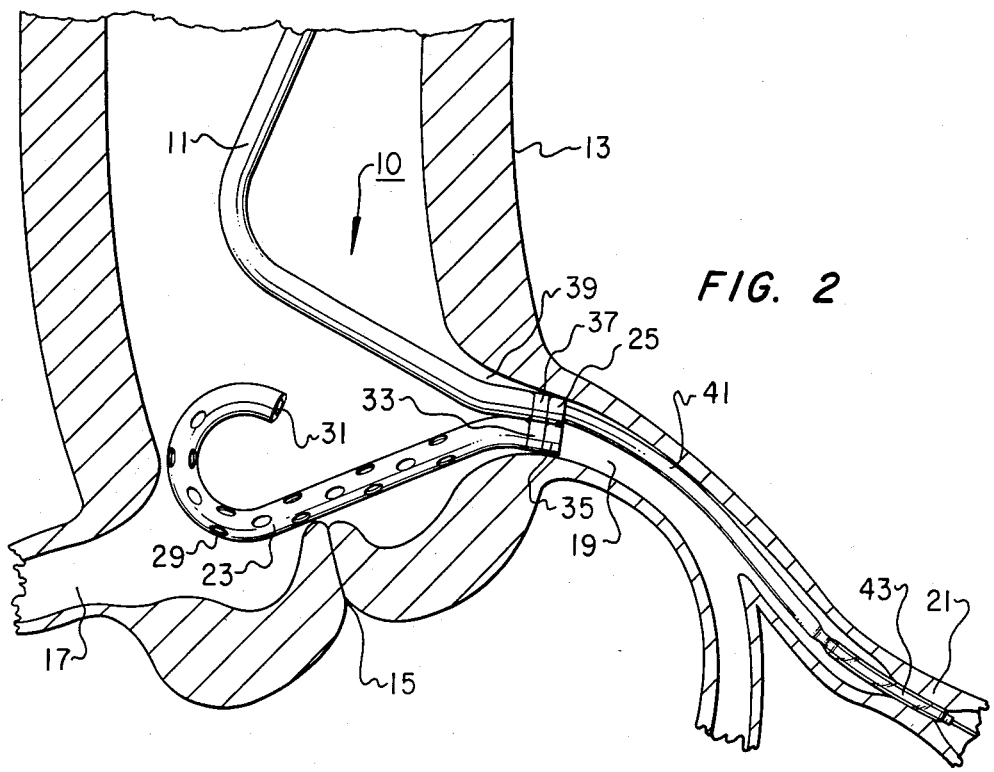
FIG. 2 is a side view of the catheter assembly of the invention, in which the tubing is shown in the second position.

FIGS. 1 and 2 show the catheter assembly 10 of the invention, inserted into a patient's aorta 13. A section of the aorta 13, the aortic valve 15, the right main coronary artery 17, and the left main coronary artery 19 are shown. A stenotic lesion 21 is shown partially blocking the left main coronary artery 19.

The catheter assembly 10 includes a guiding catheter 11 and a length of tubing 23. The tip 25 of the guiding catheter 11 is pivotably connected to the proximate end 35 of the tubing 23.

In FIG. 1, the tubing 23 is shown in a first position, in which the proximate end 35 of the tubing 23 is end to end with the tip 25 of the guiding catheter 11. A guide wire 27 extends through the tubing 23 and the guiding catheter 11 to hold the tubing 23 in the first position.

The tubing 23 has a plurality of side holes 29 along its length. Fluids can thus flow into or out of the tubing 23 through the distal end 31 or through any of the holes 29.

A metal band 33 is located on the tubing 23 near the proximate end 35. A similar metal band 37 is located on the guiding catheter 11 near the tip 25. These metal bands 33, 37 are indicators to aid the physician in locating the guiding catheter 11 and the tubing 23 within the aorta 13. The metal bands 33, 37 can be easily seen in x-rays.

In FIG. 2, the length of tubing 23 is shown in a second position. In the second position, the proximate end 35 of the tubing 23 is adjacent to tip 25 of the guiding catheter 11.

The tip 25 of the guiding catheter 11 and the proximate end 35 of the tubing 23 are inserted into the ostium 39 of the left main coronary artery 19. When the tubing 23 is in the second position, the tubing 23 is curved around the walls of the aorta 13.

Also shown in FIG. 2, a dilating catheter 41 passes through the guiding catheter 11. The dilating catheter 41 extends into the left main coronary artery 19 and through the stenotic lesion 21. An inflatable balloon 43, near the end of the dilating catheter 41, has been inflated to dilate the stenotic lesion 21.

The method of using the catheter assembly 10 involves first inserting the guide wire 27 into the guiding catheter 11 and the length of tubing 23, to hold the tubing 23 in the first position. In the first position, the proximate end 35 of the tubing 23 is end to end with the tip 25 of the guiding catheter 11, as shown in FIG. 1.

The guide wire 27, the guiding catheter 11, and the tubing 23 are then inserted through the femoral artery into the patient's aorta 13. The guide wire 27 is then removed. Next, the guiding catheter 11 is maneuvered to cause the length of tubing 23 to pivot to the second position. In the second position, the proximate end 35 of the tubing 23 is adjacent to the tip 25 of the guiding catheter 11, as shown in FIG. 2.

The proximate end 35 of the tubing 23 and the tip 25 of the guiding catheter 11 are then inserted into the ostium 39 of one of the coronary arteries 17, 19. The guiding catheter assembly 10 may also be inserted into other areas, such as the aortic valve 15 or other arteries.

When the catheter assembly 10 is in the second position, as shown in FIG. 2, coronary angiography can be performed. Dye can be inserted through the guiding catheter 11 into the artery 19, without fear of the dye leaking through a side hole, because there are no side holes in the guiding catheter 11. The guiding catheter 11 does not occlude the artery 19, because blood can flow through the tubing 23. Blood flows into the tubing 23 through the plurality of side holes 29 and the distal end 31 of the tubing 23. The blood then flows out through the proximate end 35 of the tubing 23 into the artery 19.

The catheter assembly 10 of the invention can also be used to perform percutaneous transluminal coronary angioplasty. First, the catheter assembly 10 is inserted into the ostium 39 of the artery 19, as in the method of performing coronary angiography. A dilating catheter 41 is then passed through the guiding catheter 11 into the artery 19. The dilating catheter 41 is passed through the artery 19 until the inflatable balloon 43, near the tip of the catheter 41, is located within the stenotic lesion 21. Fluid is then forced through the dilating catheter 41 to inflate the balloon 43 and to dilate the stenotic lesion 21.

The new catheter assembly 10 and the new methods of performing coronary angiography and angioplasty have several advantages over the assemblies and methods of the prior art. The tubing 23 maintains an open pathway for the flow of blood into the artery 19. The curved length of tubing 23 also adds stability to help prevent the tip 25 of the guiding catheter 11 from being forced out of the ostium 39 of the artery 19.

Only the preferred embodiment of the invention has been illustrated. It should be understood that the invention is not limited to the embodiment disclosed, but is capable of numerous rearrangements, modifications, and substitutions of parts and elements, without departing from the spirit of the invention.

I claim:

1. A catheter assembly comprising:
   a guiding catheter having a tip for insertion into a coronary lumen; and
   a length of tubing, having a proximate end connected to the guiding catheter, and being pivotable between a first position, in which the proximate end is end to end with the tip of the guiding catheter, and a second position, in which the proximate end is parallel to and adjacent to the tip of the guiding catheter.

2. A catheter assembly, as recited in claim 1, wherein the length of tubing has a plurality of side holes.

3. A catheter assembly, as recited in claim 1, further comprising a guide wire for holding the tubing in the first position until the guide wire is removed from the tubing.

4. A catheter assembly as recited in claim 1, further comprising a pair of indicators, one located near the tip of the guiding catheter and the other located near the proximate end of the tubing.

5. A catheter assembly, as recited in claim 1, wherein the tubing is curved when the tubing is in the second position.

6. A catheter assembly comprising:
   a dilating catheter;
   a guiding catheter having a tip for insertion into a coronary lumen for guiding the dilating catheter into the coronary lumen; and
   a length of tubing, having a proximate end connected to the guiding catheter, and being pivotable between a first position, in which the proximate end is end to end with the tip of the guiding catheter, and a second position, in which the proximate end is adjacent to the tip of the guiding catheter.

7. A catheter assembly, as recited in claim 6, wherein the tubing has a plurality of side holes.

8. A catheter assembly, as recited in claim 6, further comprising a guide wire for holding the tubing in the first position until the guide wire is removed from the tubing.

9. A catheter assembly as recited in claim 6, further comprising a pair of indicators, one located near the tip of the guiding catheter and the other located near the proximate end of the tubing.

10. A catheter assembly, as recited in claim 6, wherein the tubing is curved when the tubing is in the second position.

11. A method of using a catheter assembly, the method comprising the following steps in sequence:
    (a) inserting a guide wire into a guiding catheter and a length of tubing having a proximate end pivotally connected end to end to the tip of the guiding catheter;
    (b) inserting the guide wire, guiding catheter, and length of tubing into a patient's aorta;
    (c) removing the guide wire from the guiding catheter and tubing; and
    (d) maneuvering the guiding catheter to cause the tubing to pivot to a second position in which the proximate end of the tubing is adjacent to the tip of the guiding catheter.

12. A method of using a catheter assembly to perform percutaneous transluminal coronary angioplasty, the method comprising the following steps in sequence:
    (a) inserting a guide wire into a guiding catheter and a length of tubing having a proximate end pivotally connected end to end to the tip of the guiding catheter;
    (b) inserting the guide wire, guiding catheter, and length of tubing into a patient's aorta;
    (c) removing the guide wire from the guiding catheter and tubing;
    (d) maneuvering the guiding catheter to cause the tubing to pivot to a second position in which the proximate end of the tubing is adjacent to the tip of the guiding catheter;
    (e) inserting the tip of the guiding catheter and the proximate end of the tubing into a coronary lumen of a coronary artery;
    (f) passing a dilating catheter through the guiding catheter to a stenotic lesion within the coronary lumen;
    (g) inflating a balloon on the dilating catheter to dilate the stenotic lesion;
    (h) deflating the balloon; and
    (i) removing the catheters and tubing from the patient.

* * * * *